US009959746B1

United States Patent
Krishnamoorthy et al.

(10) Patent No.: US 9,959,746 B1
(45) Date of Patent: May 1, 2018

(54) SELECTIVELY DISABLING A RESTRICTED MODE OF A USER EQUIPMENT BASED ON DETECTION OF AN EMERGENCY HEALTH CONDITION

(71) Applicant: QUALCOMM Incorporated, San Diego, CA (US)

(72) Inventors: Parthasarathy Krishnamoorthy, San Diego, CA (US); Priyangshu Ghosh, Hyderabad (IN); Soumen Mitra, Hyderabad (IN); Shravan Kumar Raghunathan, San Diego, CA (US); Muthukumaran Dhanapal, San Diego, CA (US); Prashanth Mohan, Chennai (IN); Naveen Kumar Pasunooru, Hyderabad (IN); Ammar Kitabi, San Diego, CA (US); Jayesh Bathija, San Diego, CA (US); Praveen Kumar Appani, San Diego, CA (US); Hargovind Bansal, Hyderabad (IN); Sagar Shah, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days. days.

(21) Appl. No.: 15/444,263

(22) Filed: Feb. 27, 2017

(51) Int. Cl.
*A61B 5/00* (2006.01)
*G08B 25/01* (2006.01)
*G06F 19/00* (2018.01)
*G08B 21/04* (2006.01)
*H04W 4/00* (2018.01)

(52) U.S. Cl.
CPC ....... *G08B 25/016* (2013.01); *G06F 19/3418* (2013.01); *G08B 21/0461* (2013.01); *H04W 4/008* (2013.01)

(58) Field of Classification Search
CPC ....... A61B 5/0024; A61B 5/68; A61B 5/6802; A61B 5/6803
USPC ...................................... 340/539.12
See application file for complete search history.

(56) References Cited

U.S. PATENT DOCUMENTS

| 8,395,495 | B2 | 3/2013 | Raduchel |
| 8,576,828 | B1 | 11/2013 | Massey, Jr. |
| 9,350,851 | B1 | 5/2016 | Halls |
| 9,687,188 | B2 * | 6/2017 | Dugan ..................... A61B 5/18 |

(Continued)

*Primary Examiner* — Kevin Kim
(74) *Attorney, Agent, or Firm* — Muncy, Geissler, Olds & Lowe, P.C.

(57) ABSTRACT

In an embodiment, a user equipment (UE) determines an emergency health condition for a user that is defined based on a set of health-related parameters crossing a corresponding set of thresholds. The UE receives health data from a set of health monitoring sensors that are each configured to monitor one or more health-related parameters of the user. The UE detects, while a restricted mode restricting access to a set of communicative functions of the UE is active, that the emergency health condition for the user exists based on the received health data indicating that the set of health-related parameters have crossed the corresponding set of thresholds. The UE disables the restricted mode in response to the detecting. The UE conveys, using one or more communicative functions from the set of communicative functions that are made available by the disabling of the restricted mode, an alarm related to the detected emergency health condition for the user.

29 Claims, 9 Drawing Sheets

(56) References Cited

U.S. PATENT DOCUMENTS

| | | |
|---|---|---|
| 2011/0230161 A1 | 9/2011 | Newman |
| 2015/0102924 A1 | 4/2015 | Soloway et al. |
| 2015/0338917 A1* | 11/2015 | Steiner .................. H04L 9/3231 345/156 |
| 2016/0270048 A1* | 9/2016 | Kim ...................... H04W 4/008 |

* cited by examiner

SELECTIVELY DISABLING A RESTRICTED MODE OF A USER EQUIPMENT BASED ON DETECTION OF AN EMERGENCY HEALTH CONDITION

BACKGROUND

1. Field of the Disclosure

Embodiments relate to selectively disabling a restricted mode of a user equipment based on detection of an emergency health condition.

2. Description of the Related Art

Various wearable and/or internal health monitoring sensors (e.g., glucose monitor, blood pressure monitor, heart rate monitor, brainwave detector, etc.) are becoming commonplace. For example, smart pedometers (e.g., Fitbit, Apple Watch, etc.) can track not only steps, but also health-related parameters such as heart rate. Health monitoring sensors can be coupled to user equipments (UEs) such as smart phones or tablet computers to provide certain alerts (e.g., when a user reaches 10,000 steps, etc.). These alerts may also include health-related alerts. However, a UE receiving these health-related alerts may be operating in a restricted mode (e.g., Silent mode, Do-Not-Disturb mode, etc.), which limits the capability of the UE to convey the alert to the user and/or to one or more external entities.

SUMMARY

An embodiment of the disclosure is directed to a method of operating a user equipment (UE), including determining an emergency health condition for a user that is defined based on a set of health-related parameters crossing a corresponding set of thresholds, receiving health data from a set of health monitoring sensors that are each configured to monitor one or more health-related parameters of the user, detecting, while a restricted mode restricting access to a set of communicative functions of the UE is active, that the emergency health condition for the user exists based on the received health data indicating that the set of health-related parameters have crossed the corresponding set of thresholds, disabling the restricted mode in response to the detecting, and conveying, using one or more communicative functions from the set of communicative functions that are made available by the disabling of the restricted mode, an alarm related to the detected emergency health condition for the user.

An embodiment of the disclosure is directed to a UE, including means for determining an emergency health condition for a user that is defined based on a set of health-related parameters crossing a corresponding set of thresholds, means for receiving health data from a set of health monitoring sensors that are each configured to monitor one or more health-related parameters of the user, means for detecting, while a restricted mode restricting access to a set of communicative functions of the UE is active, that the emergency health condition for the user exists based on the received health data indicating that the set of health-related parameters have crossed the corresponding set of thresholds, means for disabling the restricted mode in response to the detection, and means for conveying, using one or more communicative functions from the set of communicative functions that are made available by the disabling of the restricted mode, an alarm related to the detected emergency health condition for the user.

An embodiment of the disclosure is directed to a UE, including at least one processor coupled to memory and configured to determine an emergency health condition for a user that is defined based on a set of health-related parameters crossing a corresponding set of thresholds, receive health data from a set of health monitoring sensors that are each configured to monitor one or more health-related parameters of the user, detect, while a restricted mode restricting access to a set of communicative functions of the UE is active, that the emergency health condition for the user exists based on the received health data indicating that the set of health-related parameters have crossed the corresponding set of thresholds, disable the restricted mode in response to the detection, and convey, using one or more communicative functions from the set of communicative functions that are made available by the disabling of the restricted mode, an alarm related to the detected emergency health condition for the user.

An embodiment of the disclosure is directed to a non-transitory computer-readable medium containing instructions stored thereon, which, when executed by a user equipment (UE), cause the UE to perform operations, the instructions including at least one instruction to cause the UE to determine an emergency health condition for a user that is defined based on a set of health-related parameters crossing a corresponding set of thresholds, at least one instruction to cause the UE to receive health data from a set of health monitoring sensors that are each configured to monitor one or more health-related parameters of the user, at least one instruction to cause the UE to detect, while a restricted mode restricting access to a set of communicative functions of the UE is active, that the emergency health condition for the user exists based on the received health data indicating that the set of health-related parameters have crossed the corresponding set of thresholds, at least one instruction to cause the UE to disable the restricted mode in response to the detection, and at least one instruction to cause the UE to convey, using one or more communicative functions from the set of communicative functions that are made available by the disabling of the restricted mode, an alarm related to the detected emergency health condition for the user.

BRIEF DESCRIPTION OF THE DRAWINGS

A more complete appreciation of embodiments of the disclosure will be readily obtained as the same becomes better understood by reference to the following detailed description when considered in connection with the accompanying drawings which are presented solely for illustration and not limitation of the disclosure, and in which.

DETAILED DESCRIPTION

Figure 1:
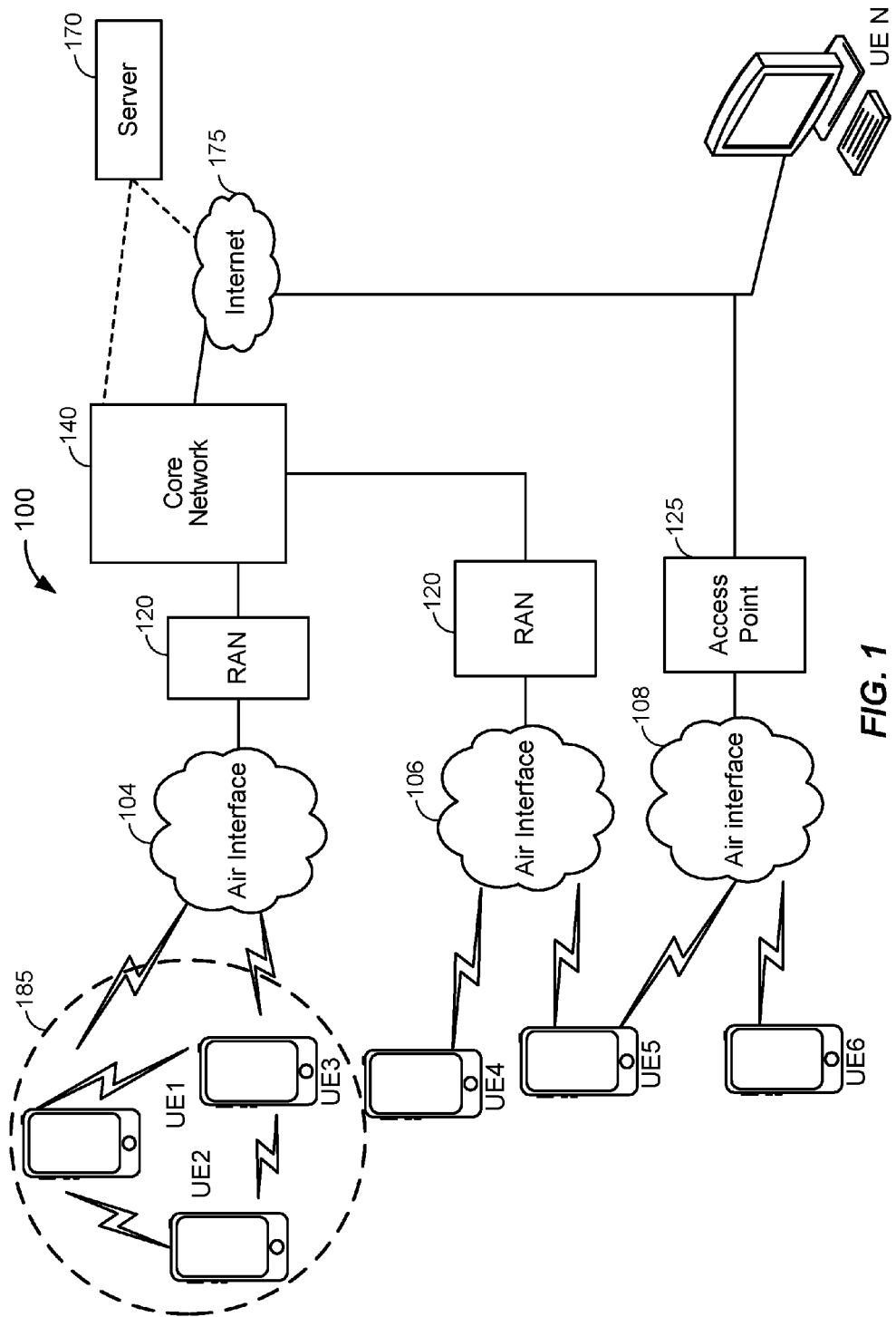
FIG. 1 illustrates a high-level system architecture of a wireless communications system in accordance with an embodiment of the disclosure.

Embodiments of the disclosure relate to selectively disabling (or overriding) a restricted mode of a user equipment (UE) based on detection of an emergency health condition. As will be described below in more detail, the UE may detect the emergency health condition based on health data received from one or more health monitoring sensors while the UE is operating in the restricted mode, which causes the UE to disable the restricted mode at least in part in order to convey an alarm related to the detected emergency health condition. The alarm may be conveyed by the UE locally (e.g., via speakers, a display coupled to or integrated into the UE, etc.) and/or may be conveyed to one or more external entities (e.g., proximate UEs, particular contacts of the user and/or emergency response personnel).

Aspects of the disclosure are disclosed in the following description and related drawings directed to specific embodiments of the disclosure. Alternate embodiments may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any embodiment described herein as "exemplary" and/or "example" is not necessarily to be construed as preferred or advantageous over other embodiments. Likewise, the term "embodiments of the disclosure" does not require that all embodiments of the disclosure include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

A client device, referred to herein as a user equipment (UE), may be mobile or stationary, and may communicate with a wired access network and/or a radio access network (RAN). As used herein, the term "UE" may be referred to interchangeably as an "access terminal" or "AT", a "wireless device", a "subscriber device", a "subscriber terminal", a "subscriber station", a "user terminal" or UT, a "mobile device", a "mobile terminal", a "mobile station" and variations thereof. In an embodiment, UEs can communicate with a core network via the RAN, and through the core network the UEs can be connected with external networks such as the Internet. Of course, other mechanisms of connecting to the core network and/or the Internet are also possible for the UEs, such as over wired access networks, WiFi networks (e.g., based on IEEE 802.11, etc.) and so on. UEs can be embodied by any of a number of types of devices including but not limited to cellular telephones, personal digital assistants (PDAs), pagers, laptop computers, desktop computers, PC cards, compact flash devices, external or internal modems, wireless or wireline phones, and so on. A communication link through which UEs can send signals to the RAN is called an uplink channel (e.g., a reverse traffic channel, a reverse control channel, an access channel, etc.). A communication link through which the RAN can send signals to UEs is called a downlink or forward link channel (e.g., a paging channel, a control channel, a broadcast channel, a forward traffic channel, etc.). A communication link through which UEs can send signals to other UEs is called a peer-to-peer (P2P) or device-to-device (D2D) channel.

FIG. 1 illustrates a high-level system architecture of a wireless communications system 100 in accordance with an embodiment of the disclosure. The wireless communications system 100 contains UEs 1 . . . N. For example, in FIG. 1, UEs 1 . . . 2 are illustrated as cellular calling phones, UEs 1 . . . 6 are illustrated as cellular touchscreen phones or smart phones, and UE N is illustrated as a desktop computer or PC.

Referring to FIG. 1, UEs 1 . . . N are configured to communicate with an access network (e.g., a RAN 120, an access point 125, etc.) over a physical communications interface or layer, shown in FIG. 1 as air interfaces 104, 106, 108 and/or a direct wired connection. The air interfaces 104 and 106 can comply with a given cellular communications protocol (e.g., CDMA, EVDO, eHRPD, GSM, EDGE, W-CDMA, 4G LTE, 5G LTE, etc.), while the air interface 108 can comply with a wireless IP protocol (e.g., IEEE 802.11). The RAN 120 may include a plurality of access points that serve UEs over air interfaces, such as the air interfaces 104 and 106. The access points in the RAN 120 can be referred to as access nodes or ANs, access points or APs, base stations or BSs, Node Bs, eNode Bs, and so on. These access points can be terrestrial access points (or ground stations), or satellite access points. The RAN 120 may be configured to connect to a core network 140 that can perform a variety of functions, including bridging circuit switched (CS) calls between UEs served by the RAN 120 and other UEs served by the RAN 120 or a different RAN altogether, and can also mediate an exchange of packet-switched (PS) data with external networks such as Internet 175.

The Internet 175, in some examples includes a number of routing agents and processing agents (not shown in FIG. 1 for the sake of convenience). In FIG. 1, UE N is shown as connecting to the Internet 175 directly (i.e., separate from the core network 140, such as over an Ethernet connection of WiFi or 802.11-based network). The Internet 175 can thereby function to bridge packet-switched data communications between UEs 1 . . . N via the core network 140. Also shown in FIG. 1 is the access point 125 that is separate from the RAN 120. The access point 125 may be connected to the Internet 175 independent of the core network 140 (e.g., via an optical communications system such as FiOS, a cable modem, etc.). The air interface 108 may serve UE 5 or UE 6 over a local wireless connection, such as IEEE 802.11 in an example. UE N is shown as a desktop computer with a wired connection to the Internet 175, such as a direct connection to a modem or router, which can correspond to the access point 125 itself in an example (e.g., for a WiFi router with both wired and wireless connectivity).

Referring to FIG. 1, a server 170 is shown as connected to the Internet 175, the core network 140, or both. The server 170 can be implemented as a plurality of structurally separate servers, or alternately may correspond to a single server. The server 170 may correspond to any type of server, such as a web server (e.g., hosting a web page), an application download server, or an application server that supports particular communicative service(s), such as Voice-over-Internet Protocol (VoIP) sessions, Push-to-Talk (PTT) sessions, group communication sessions, a social networking service, etc.

Referring to FIG. 1, UEs 1 . . . 3 are depicted as part of a D2D network or D2D group 185, with UEs 1 and 3 being connected to the RAN 120 via the air interface 104. In an embodiment, UE 2 may also gain indirect access to the RAN 120 via mediation by UEs 1 and/or 3, whereby data 'hops' to/from UE 2 and one (or more) of UEs 1 and 3, which communicate with the RAN 120 on behalf of UE 2.

Figure 2:
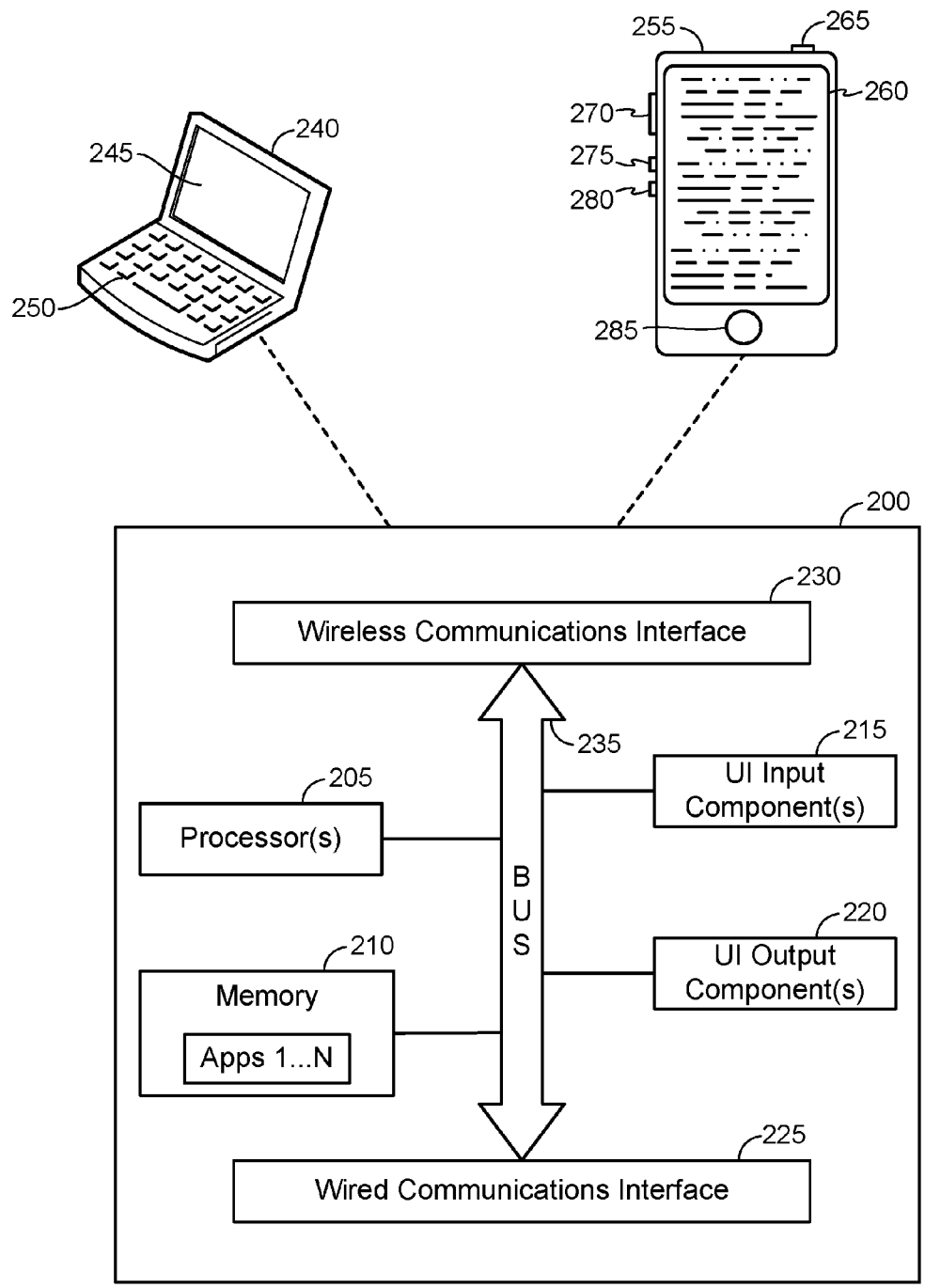
FIG. 2 illustrates a user equipment (UE) in accordance with an embodiment of the disclosure.

FIG. 2 illustrates a UE 200 in accordance with an embodiment of the disclosure. The UE 200 includes one or more processors 205 (e.g., one or more ASICs, one or more digital signal processors (DSPs), etc.) and a memory 210 (e.g., RAM, ROM, EEPROM, flash cards, or any memory common to computer platforms). The memory 210 includes a plurality of applications 1 . . . N that are executable by the one or more processors 205 via an associated operating system. The UE 200 also includes one or more UI input components 215 (e.g., a keyboard and mouse, a touchscreen, a microphone, one or more buttons such as volume or power buttons, etc.) and one or more UI output components 220 (e.g., speakers, a display screen, a vibration device for vibrating the UE 200, etc.).

The UE 200 further includes a wired communications interface 225 and a wireless communications interface 230. In an example embodiment, the wired communications interface 225 can be used to support wired local connections to peripheral devices (e.g., a USB connection, a mini USB, Firewire or lightning connection, a headphone jack, graphics ports such as serial, VGA, HDMI, DVI or DisplayPort, audio ports, and so on) and/or to a wired access network (e.g., via an Ethernet cable or another type of cable that can function as a bridge to the wired access network such as HDMI v1.4 or higher, etc.). In another example embodiment, the wireless communications interface 230 includes one or more wireless transceivers for communication in accordance with a local wireless communications protocol (e.g., WLAN or WiFi, WiFi Direct, Bluetooth, LTE-D, Miracast, etc.). The wireless communications interface 225 may also include one or more wireless transceivers for communication with a cellular RAN (e.g., via CDMA, W-CDMA, time division multiple access (TDMA), frequency division multiple access (FDMA), Orthogonal Frequency Division Multiplexing (01-DM), GSM, or other protocols that may be used in a wireless communications network or a data communications network). The various components 205-230 of the UE 200 can communicate with each other via a bus 235.

Referring to FIG. 2, the UE 200 may correspond to any type of UE, including but not limited to a smart phone, a laptop computer, a desktop computer, a tablet computer, a wearable device (e.g., a pedometer, a smart watch, etc.) and so on. Two particular implementation examples of the UE 200 are depicted in FIG. 2, which are illustrated as laptop 240 and touchscreen device 255 (e.g., a smart phone, a tablet computer, etc.). The laptop 240 includes a display screen 245 and a UI area 250 (e.g., keyboard, touchpad, power button, etc.), and while not shown the laptop 240 may include various ports as well as wired and/or wireless transceivers (e.g., Ethernet card, WiFi card, broadband card, satellite position system (SPS) antennas such as global positioning system (GPS) antennas, etc.).

The touchscreen device 255 is configured with a touchscreen display 260, peripheral buttons 265, 270, 275 and 280 (e.g., a power button, a volume or vibrate control button, an airplane mode toggle button, etc.), and at least one front-panel button 285 (e.g., a Home button, etc.), among other components, as is known in the art. While not shown explicitly as part of the touchscreen device 255, the touchscreen device 255 can include one or more external antennas and/or one or more integrated antennas that are built into the external casing of the touchscreen device 255, including but not limited to WiFi antennas, cellular antennas, SPS antennas (e.g., GPS antennas), and so on.

Figure 3:
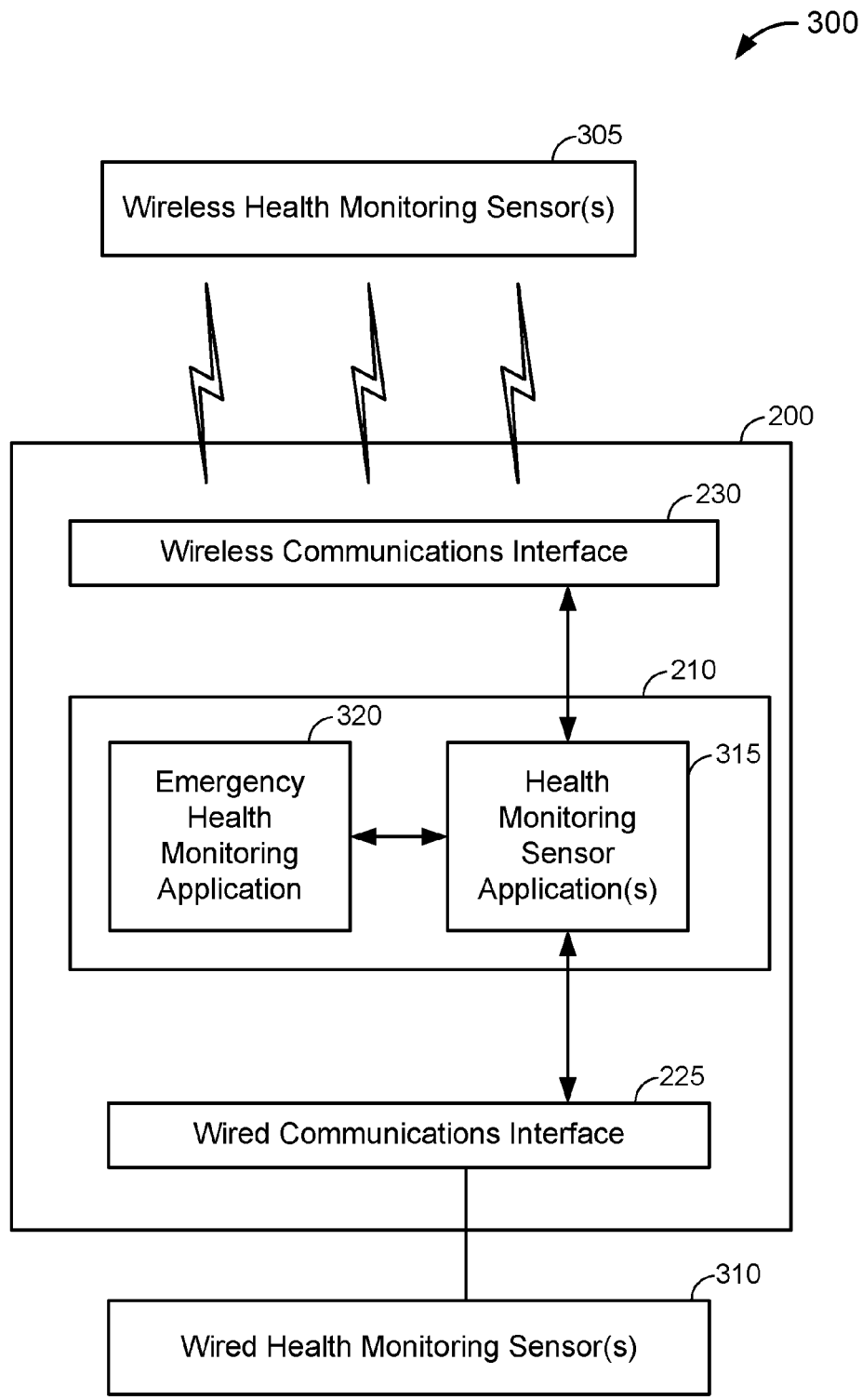
FIG. 3 illustrates a health monitoring system in accordance with another embodiment of the disclosure.

FIG. 3 illustrates a health monitoring system 300 in accordance with another embodiment of the disclosure. In FIG. 3, the health monitoring system includes UE 200, a set of wireless health monitoring sensors 305 coupled to UE 200 via the wireless communications interface 230 (e.g., via Bluetooth, Wi-Fi, LTE-D, NFC, etc.) and a set of wired health monitoring sensors 310 coupled to UE 200 via the wired communications interface 310 (e.g., via USB, etc.). In FIG. 3, certain components of UE 200 that are shown in FIG. 2 are omitted for convenience of illustration (e.g., the processor(s) 205, etc.). Also, while the health monitoring system 300 of FIG. 3 depicts both wired and wireless health monitoring sensors, this is intended to show the range of sensor options, and other embodiments may include wireless health monitoring sensor only or wired health monitoring sensors only.

Referring to FIG. 3, each health monitoring sensor that belongs to the set of wireless health monitoring sensors 305 and/or the set of wired health monitoring sensors 310 is configured to monitor one or more health-related parameters of the user (e.g., glucose level, blood pressure, heart rate, brainwave activity, etc.). For example, the set of wireless health monitoring sensors 305 and/or the set of wired health monitoring sensors 310 may include a glucose monitor (e.g., a continuous glucose monitor), a heart rate monitor (e.g., a wearable device such as a Fitbit or Apple Watch, or an internally-integrated device such as a pacemaker), a brainwave detector, or any combination thereof. Accordingly, the health monitoring sensors may be attached to (e.g., worn by) the user, or can actually be internally-integrated (or fit into) the user.

Referring to FIG. 3, the set of wireless health monitoring sensors 305 and the set of wired health monitoring sensors 310 provide health data based on their respective monitoring functions to at least one corresponding health monitoring sensor application 315 on UE 200. The health monitoring sensor application(s) 315 provide some or all of the health data with an emergency health condition monitoring application 320, which is configured to interpret the health data to detect whether a user of UE 200 is experiencing an emergency health condition, as will be described below in more detail. In an example, the emergency health condition monitoring application 320 may be integrated into modem software of UE 200, such as part of a real-time OS (RTOS) of UE 200.

In an example, the health monitoring sensor application(s) 315 may include separate dedicated applications for each respective health monitoring sensor (e.g., a glucose application for interfacing with a glucose monitor (e.g., a continuous glucose monitor), a heart rate application for interfacing with a heart rate application, and so on). Alternatively, two or more health monitoring sensors may interface with a common health monitoring sensor application. In a further example, the health monitoring sensor application(s) 315 may be implemented as third-party executable applications or alternatively may be integrated into modem software of UE 200, such as a RTOS. Further, while depicted as separate applications, the health monitoring sensor application(s) 315 and the emergency health condition monitoring application 320 may alternatively be incorporated as modules of one particular executable application among the applications stored in the memory 210 of UE 200 (e.g., as OS-level or as a third-party application).

Figure 4:
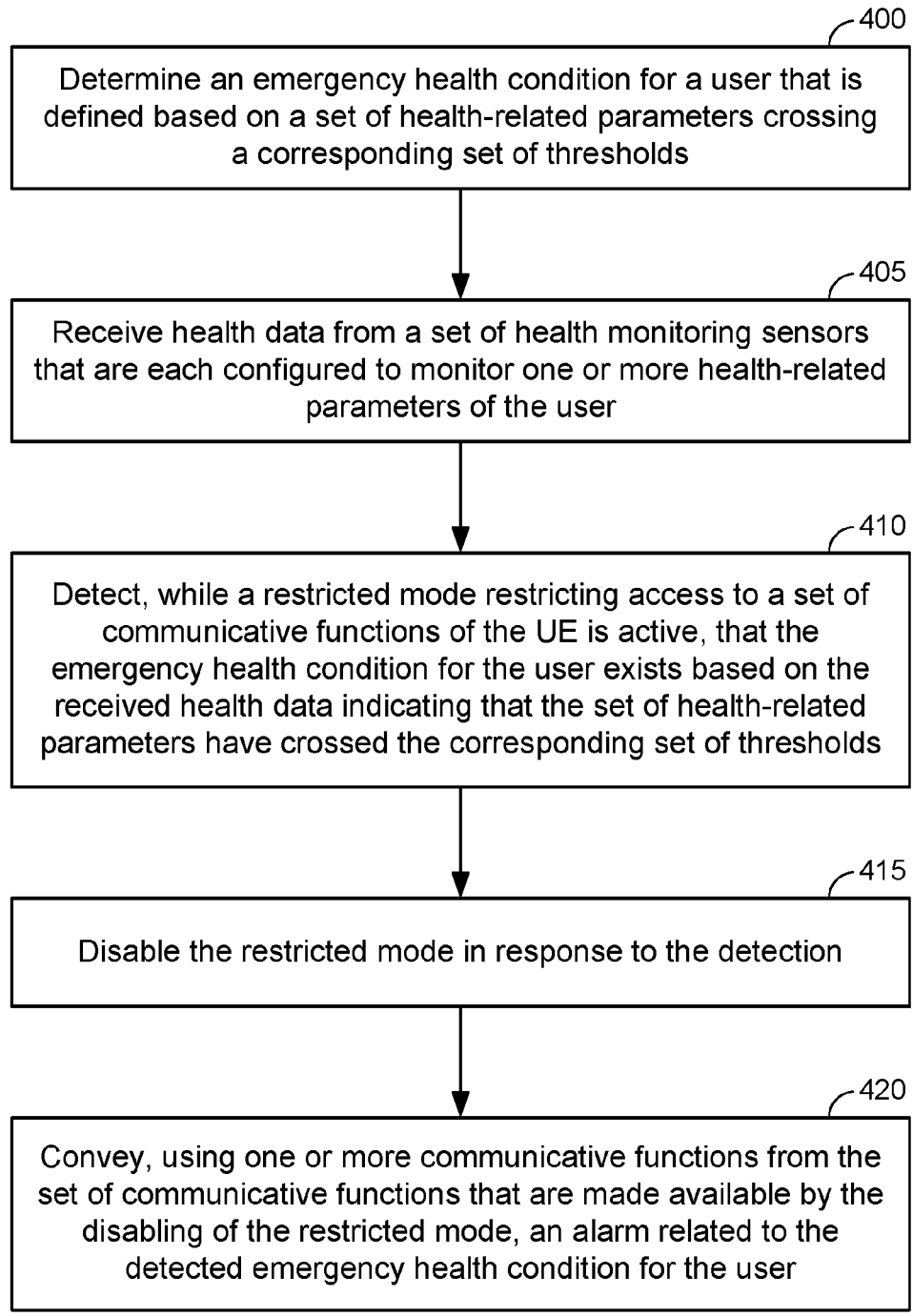
FIG. 4 illustrates a process of selectively disabling a restricted mode of a UE in accordance with an embodiment of the disclosure.

FIG. 4 illustrates a process of selectively disabling a restricted mode of a UE in accordance with an embodiment of the disclosure. The process of FIG. 4 may be performed at a UE, such as UE 200 as described above with respect to FIGS. 2-3.

Referring to FIG. 4, at block 400, the UE determines an emergency health condition for a user that is defined based on a set of health-related parameters crossing a corresponding set of thresholds. As an example, the determination at block 400 can be based upon user input, as shown in FIG. 5A.

Figure 5A:
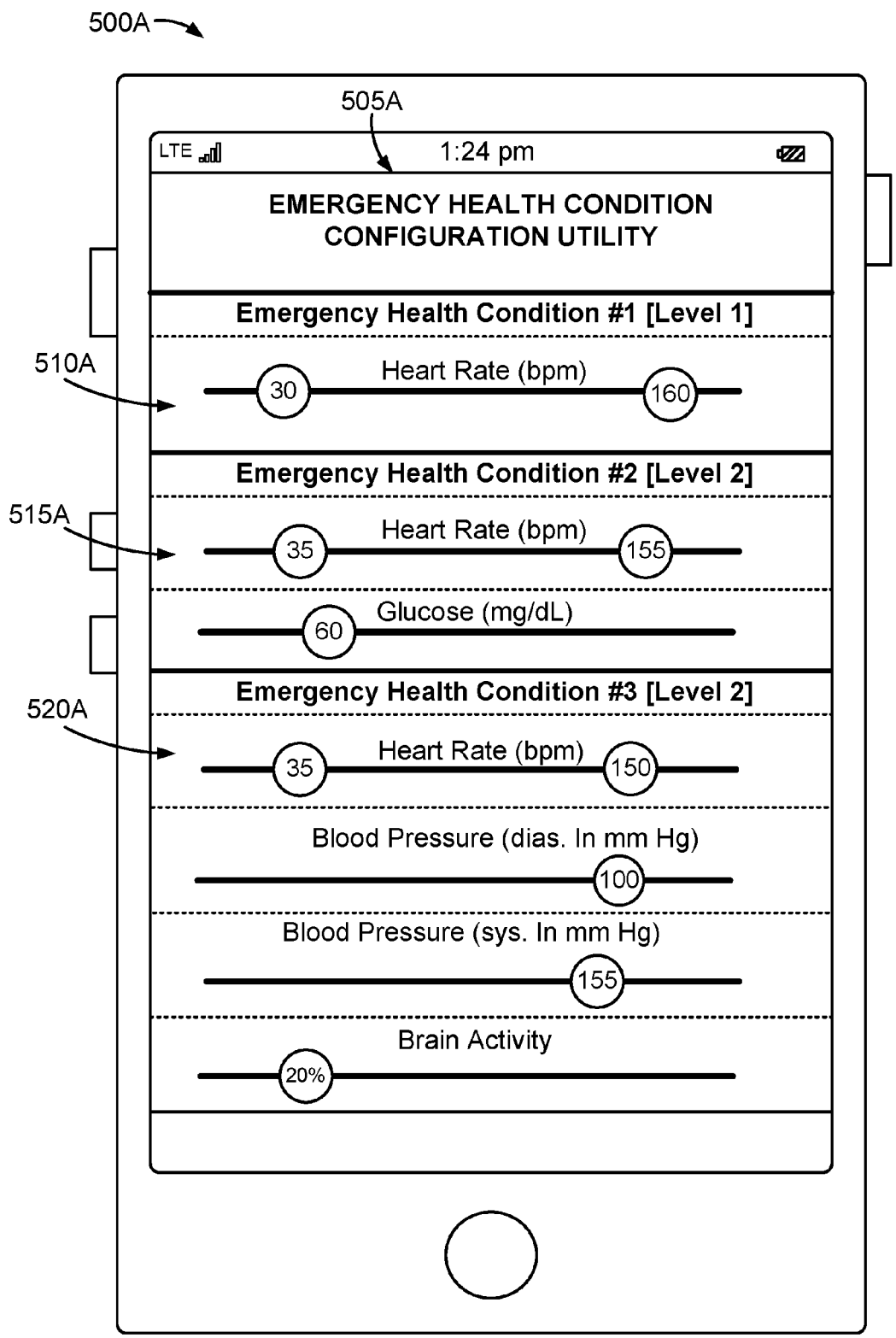
FIG. 5A depicts a UE that has opened an emergency health condition configuration utility screen in accordance with an embodiment of the disclosure.

FIG. 5A depicts a UE 500A (e.g., a smartphone, a tablet computer, etc.) that has opened an emergency health condition configuration utility screen 505A. In an example, the emergency health condition configuration utility screen 505A may be implemented as part of the emergency health condition monitoring application 320 of FIG. 3. The emergency health condition configuration utility screen 505A defines, with respect to 510A, 510A and 515A, particular sets of health-related parameters and corresponding threshold(s) for three distinct emergency health conditions #1, #2 and #3, respectively.

Referring to FIG. 5A, emergency health condition #1 is defined as shown at 510A based on a heart rate parameter only, with a lower threshold specified as 30 beats per minute (bpm) and an upper threshold specified as 160 bpm. During operation, emergency health condition #1 is detected whenever the heart rate of the user under observation falls under the lower threshold (30 bpm) or rises above the upper threshold (160 bpm). While not illustrated in FIG. 5A, other heart rate conditions (e.g., arrhythmia, etc.) may also be monitored as a health-related parameter for any of the emergency health conditions depicted in FIG. 5A.

Referring to FIG. 5A, emergency health condition #2 is defined as shown at 515A based on a combination of heart rate parameter and glucose level parameter. In emergency health condition #2, the heart rate parameter includes a lower threshold (35 bpm) and an upper threshold (155 bpm), and the glucose level parameter is defined with a single threshold (60 milligrams/deciliter or mg/dL). During operation, emergency health condition #2 is detected whenever (i) the heart rate of the user under observation falls under the lower threshold (35 bpm) or rises above the upper threshold (155 bpm), and (ii) the glucose level of the user falls below 60 mg/dL. While not shown in FIG. 5A, the glucose level parameter for emergency health condition #2 could also include an upper threshold, but this can be omitted based on user preference (e.g., the user is only concerned with glucose level dropping too low and not worried about high glucose levels). Also, another user may configure an emergency health condition with an upper threshold and no lower threshold (e.g., if that user is only concerned with high glucose levels). Similarly the heart rate parameter can be configured with only a single threshold to monitor for high heart rate only or low heart rate only (instead of both).

Referring to FIG. 5A, emergency health condition #3 is defined as shown at 520A based on a combination of heart rate parameter, different blood pressure parameters and a brain activity parameter. In emergency health condition #3, the heart rate parameter includes a lower threshold (35 bpm) and an upper threshold (150 bpm), a first blood pressure parameter for diastolic is defined with a single threshold (100 millimeters of mercury or mmHg), a second blood pressure parameter for systolic is defined with a single threshold (155 mmHg), and a brainwave activity parameter is defined with a single threshold of 20%. During operation, emergency health condition #3 is detected whenever (i) the heart rate of the user under observation falls under the lower threshold (35 bpm) or rises above the upper threshold (150 bpm), (ii) the diastolic blood pressure of the user rises above 100 mmHg, (iii) the systolic blood pressure of the user rises above 155 mmHg and (iv) the brain activity of the user falls below 20%.

As will be appreciated, the various emergency health conditions depicted in FIG. 5A are provided for example purposes only, as any combination of health-related parameters can be part of emergency health conditions in other embodiments of the disclosure. Also, the emergency health condition configuration utility screen 505A may start out blank and require the user to customize each emergency health condition, or alternatively certain default emergency health conditions may be available which permit user customization (e.g., a user can use the various thresholds depicted in FIG. 5A as sliders to shift thresholds to desired levels). Accordingly, in certain embodiments, some thresholds for particular emergency health conditions may be user-defined, while others may be set to default or system-defined levels.

Further, the particular types of health-related parameters that define the respective emergency health conditions may also be user customizable. In other words, the emergency health condition configuration utility screen 505A may allow the user may to add and/or remove health-related parameters to particular emergency health conditions. The user may also add and/or remove emergency health conditions. Various system-defined or community-sourced emergency health conditions may also be downloaded to the UE from an external source, or made available via an emergency health condition library stored in local memory at the UE.

Referring to FIG. 4, at block 405, the UE receives health data from a set of health monitoring sensors that are each configured to monitor one or more health-related parameters of the user. For example, the health data may be received from wireless and/or wired health monitoring sensors as discussed above with respect to FIG. 3.

Referring to FIG. 4, at block 410, the UE detects, while a restricted mode restricting access to a set of communicative functions of the UE is active, that the emergency health condition for the user exists based on the received health data indicating that the set of health-related parameters have crossed the corresponding set of thresholds. With respect to block 410, the restricted mode may include any mode of operation whereby one or more communicative functions of the UE are disabled, including any of the following:
- A Do-Not-Disturb (DND) mode (e.g., a mode that blocks speaker output and/or vibratory output, etc.),
- A silent mode (e.g., vibrate-only mode that blocks speaker output),
- A Wi-Fi disabled mode (e.g., a mode that blocks Wi-Fi communications),
- A cellular-disabled mode (e.g., a mode that blocks cellular communications), or
- Any combination thereof.

In an example, with respect to block 410, the detection that the emergency health condition for the user exists may be based upon a comparison between the received health data with the various emergency health condition configurations, such as those depicted in FIG. 5A with respect to 510A through 515A. It is also possible that multiple emergency health conditions are detected at block 410, as different emergency health conditions need not be mutually exclusive (e.g., a user may be having a low heart rate caused by low glucose levels, such that emergency health conditions #1 and #2 of FIG. 5A can occur concurrently)

Referring to FIG. 4, at block 415, the UE disables the restricted mode in response to the detection. The disablement at block 415 may correspond to either complete or partial disablement of the restrictive mode. For example, a UE may be set to silent mode (no speaker output) while also being set to Wi-Fi only mode (no cellular communications). For example, if the UE only needs to provide an emergency health condition alarm, then at block 415, the UE may disable silent mode to permit an audio alarm to be output by the UE while maintaining the Wi-Fi only mode because cellular communications are not required. Alternatively, in another example, the UE may fully disable both the silent mode and the Wi-Fi only mode at block 415 (e.g., if an audio alarm is to be output in tandem with an alarm notification being sent to one or more external entities).

In a further example, the disablement of the restricted mode at block 415 may be implemented in a selective manner. For example, the disablement of block 415 may only be authorized for particular application types, with the UE verifying that a particular application that is requesting disablement of the restricted mode (e.g., such as the emergency health condition monitoring application 320) has permission to disable the restricted mode before performing block 415. As an example, restricted mode override authorizations can be based upon user input, as shown in FIG. 5B.

Figure 5B:
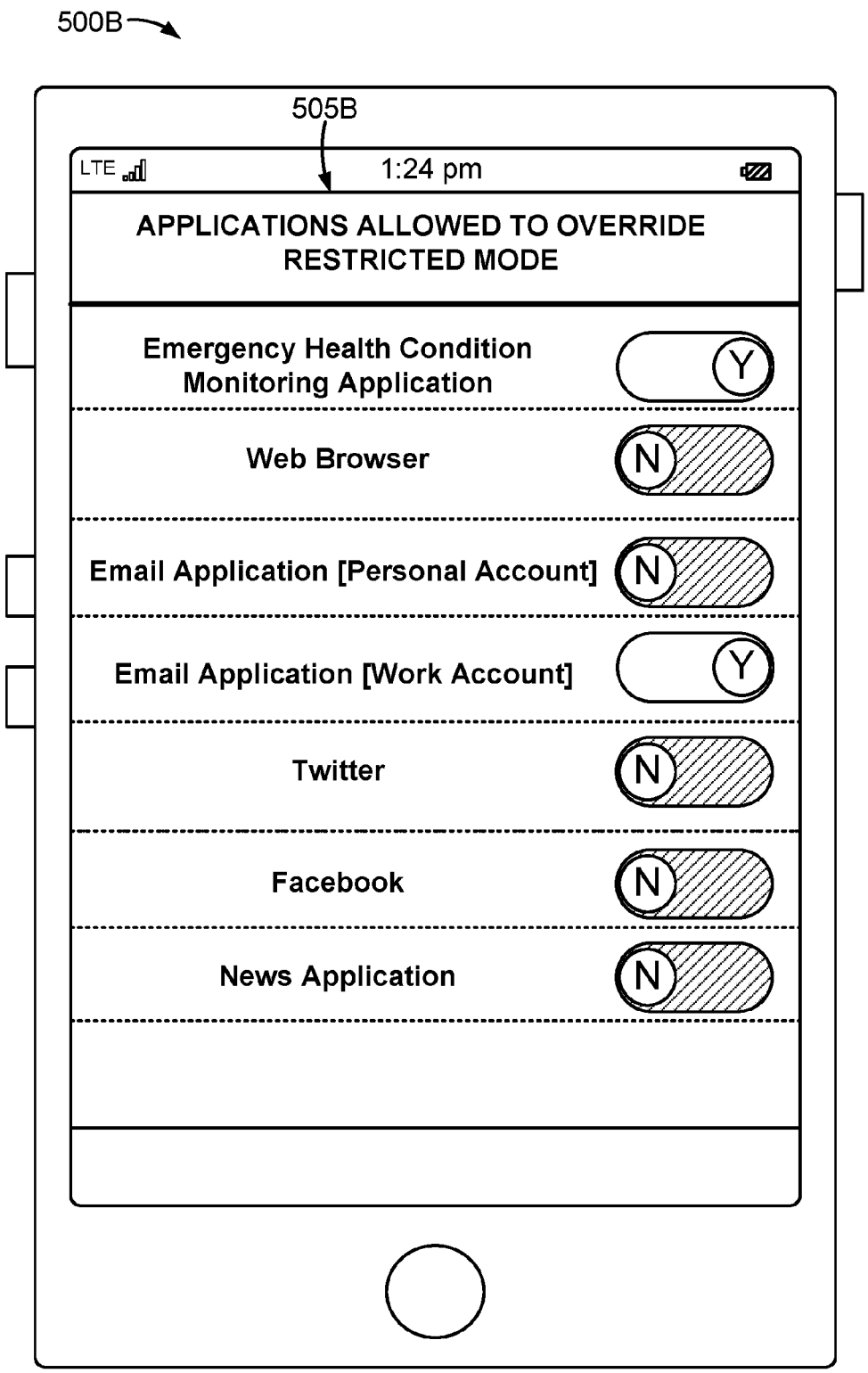
FIG. 5B depicts a UE that has opened a restricted mode override utility screen in accordance with another embodiment of the disclosure.

FIG. 5B depicts a UE 500B (e.g., a smartphone, a tablet computer, etc.) that has opened a restricted mode override utility screen 505B. In an example, the restricted mode override utility screen 505B may be implemented at the OS-level of UE 500B. As shown in the restricted mode override utility screen 505B, the user can select which applications are permitted to override the restricted mode. While not shown in FIG. 5B, the user may also selects particular communicative functions that the authorized applications are permitted to use (e.g., a work account email application may be permitted to override DND mode to provide an audio alert, but not to access Wi-Fi, while the emergency health condition monitoring application may be permitted to obtain access to any desired communicative function without restriction, etc.).

Referring to FIG. 4, at block 420, the UE conveys, using one or more communicative functions that are made available by the disabling of the restricted mode, an alarm related to the detected emergency health condition for the user. In an example, the alarm conveyance at block 420 may include outputting the alarm by the UE locally (e.g., via an audio alert, a vibratory alert, etc.), transmitting the alarm to one or more external devices, or both.

Referring to block 420 of FIG. 4, the alarm may be conveyed to one or more external devices in a variety of ways, including (i) transmitting the alarm to a set of predetermined contacts of the user, (ii) broadcasting the alarm to any in-range UE via a wireless communications protocol (e.g., a D2D protocol such as LTE-D, etc.), (iii) transmitting the alarm to emergency response personnel (e.g., sending a distress signal to a 911 operator), or (iv) any combination thereof.

In the case of a contact-specific alarm transmission, the contacts may correspond to proximate UEs (e.g., in-range of a D2D wireless communications protocol such as LTE-D) or remote UEs (e.g., communication only possible via a communications network of some type). Accordingly, the alarm to the set of predetermined contacts of the user may be transmitted via a local or D2D wireless communication protocol, a network-based communications protocol (e.g., cellular, Wi-Fi, etc.), or some combination thereof. Moreover, the UE may maintain a list of contacts (which may be defined or configured by the user in advance of the emergency health condition detection at block 410) so the UE knows which contacts need to be notified in the event of emergency health condition detection.

The particular alarm conveyance actions to be enforced by the UE in response to detection of an emergency health condition at block 410 may be predefined by the system, user-defined or some combination thereof (e.g., default alarm actions may be preconfigured, with the user given the option to customize the default alarm actions). Examples of user-configured alarm responses to be implemented at block 420 of FIG. 4 are depicted in FIGS. 6A-6B with respect to the emergency health conditions #1, #2 and #3 described above with respect to FIG. 5A.

In FIG. 5A, the emergency health conditions #1, #2 and #3 are characterized as either Level 1 or Level 2. In other embodiments, a single level may be used, or alternatively additional levels may be used. The level designation of the emergency health conditions is used to refer to the particular alarm reaction to be implemented by the UE in response to a detection of an emergency health condition at that particular level. Generally, higher level emergency health conditions are more serious and are associated with a more robust (or widespread) alarm reaction. FIG. 6A depicts an example alarm reaction for a Level 1 emergency health condition in accordance with an embodiment of the disclosure, while FIG. 6B depicts an example alarm reaction for a Level 2 emergency health condition in accordance with an embodiment of the disclosure.

Figure 6A:
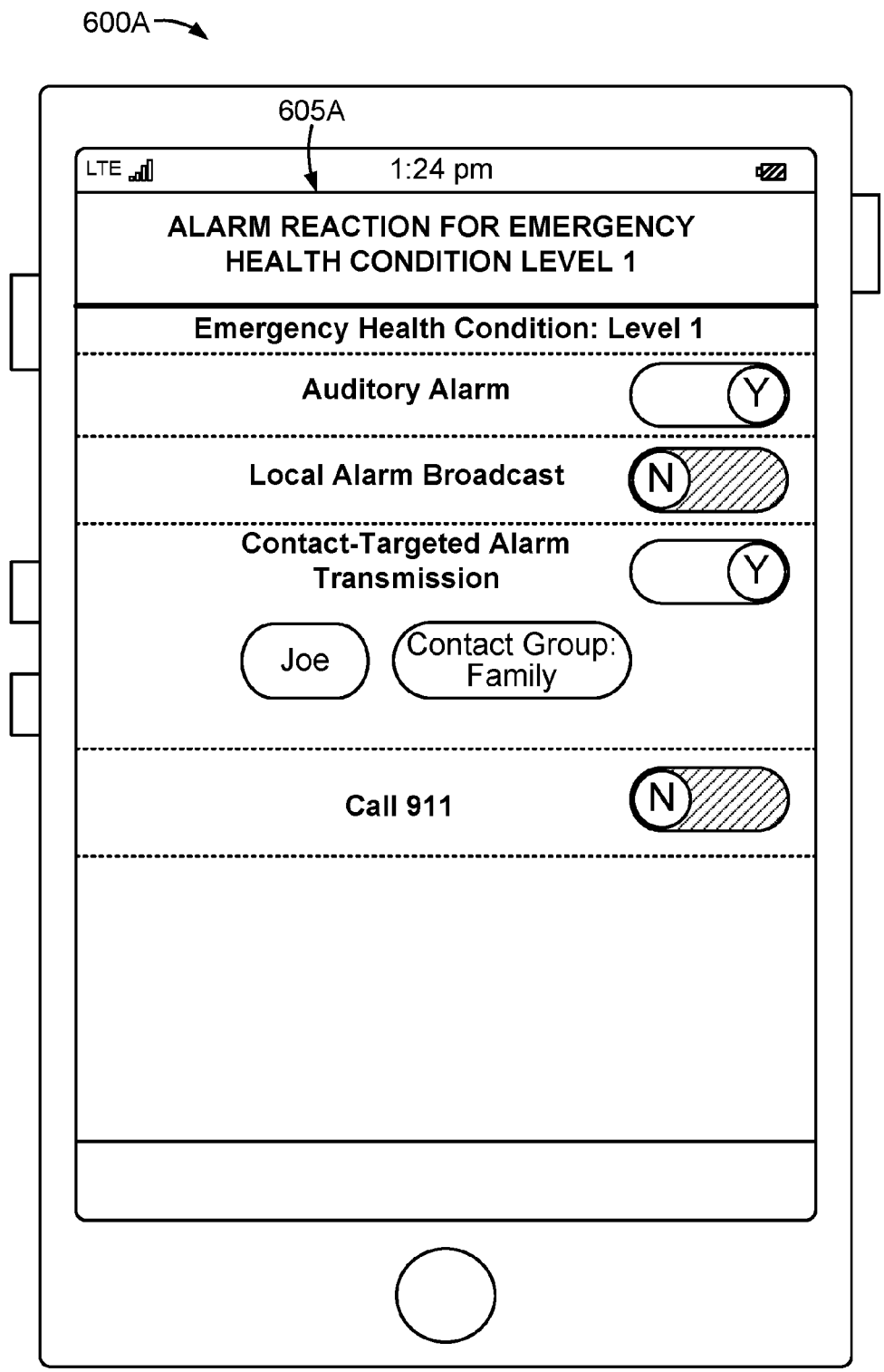
FIG. 6A depicts a UE that has opened an alarm reaction configuration utility screen in accordance with an embodiment of the disclosure.

FIG. 6A depicts a UE 600A (e.g., a smartphone, a tablet computer, etc.) that has opened an alarm reaction configuration utility screen 605A. In FIG. 6A, the alarm reaction for a Level 1 emergency health condition includes an auditory alarm and a contact-targeted alarm transmission to a contact named Joe as well as each contact in a Family contact group (e.g., containing one or more family contacts of the user). The alarm reaction for the Level 1 emergency health condition as configured in FIG. 6A excludes the local alarm broadcast option and the call 911 option (or contact emergency response personnel option).

Figure 6B:
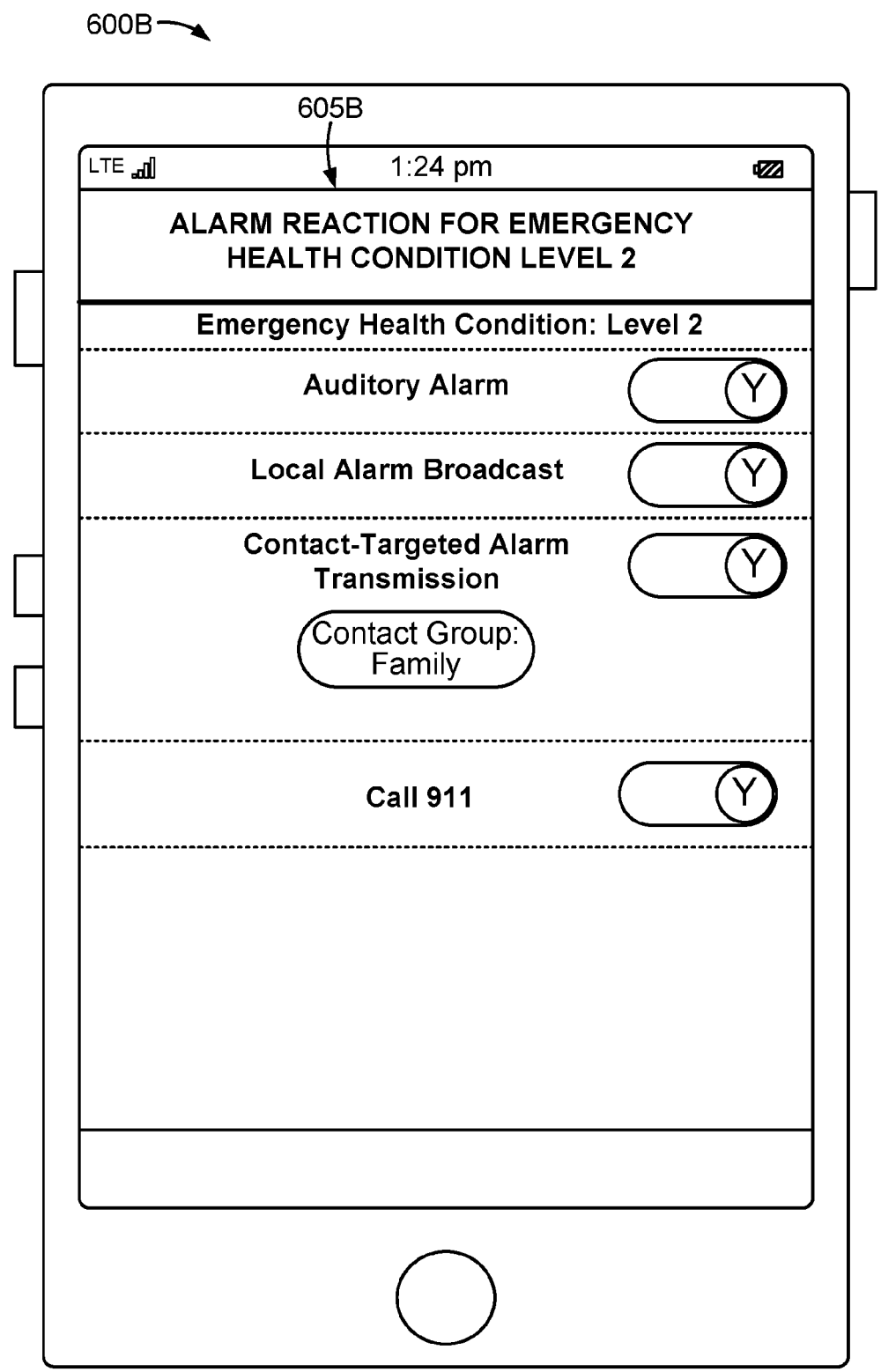
FIG. 6B depicts a UE has opened an alarm reaction configuration utility screen in accordance with another embodiment of the disclosure.

FIG. 6B depicts a UE 600B (e.g., a smartphone, a tablet computer, etc.) that has opened an alarm reaction configuration utility screen 605B. In FIG. 6B, the alarm reaction for a Level 2 emergency health condition includes an auditory alarm and a contact-targeted alarm transmission to a Family contact group (e.g., containing one or more family contacts of the user), as well as the local alarm broadcast option and the call 911 option (or contact emergency response personnel option).

Figure 7:
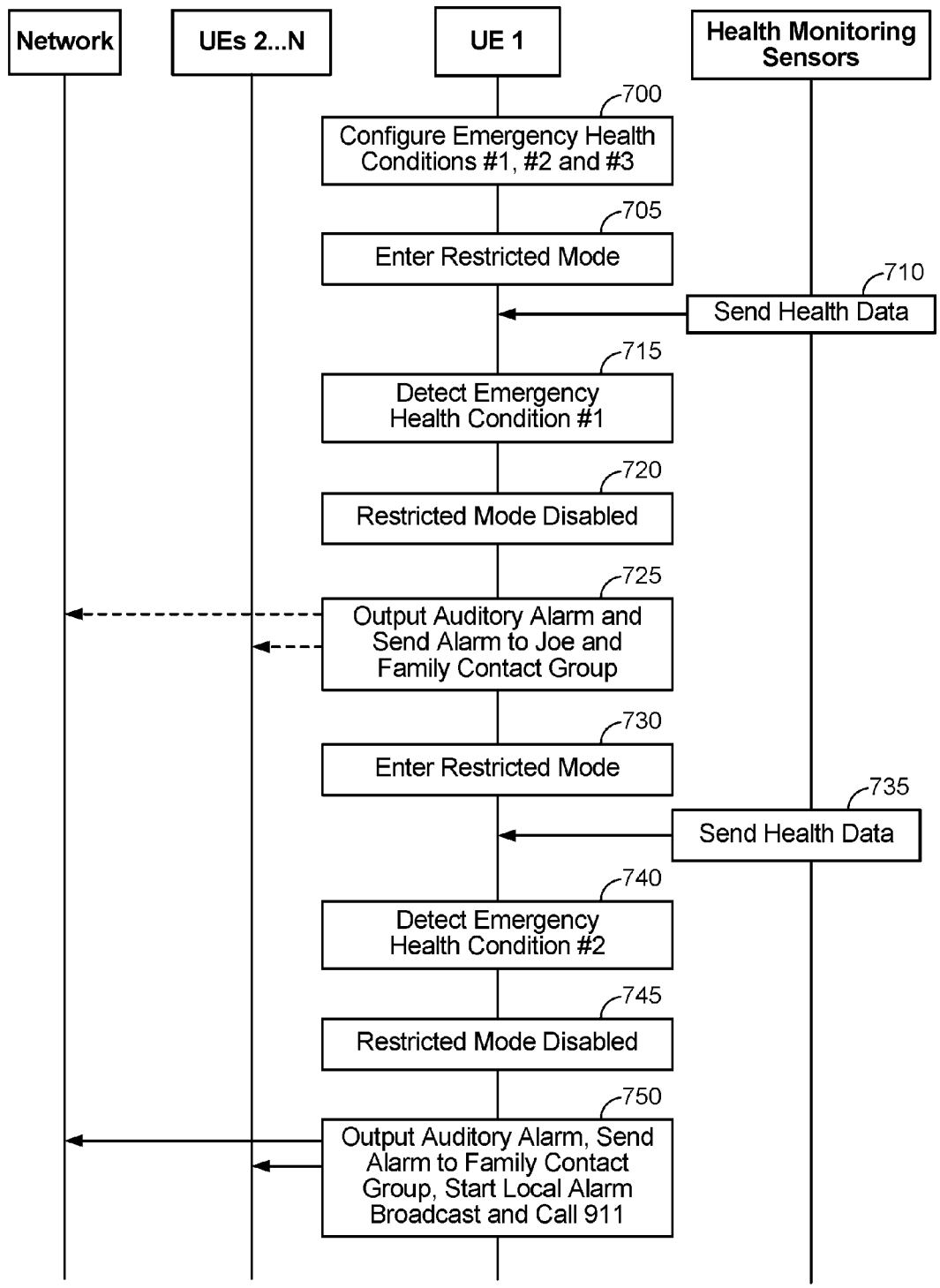
FIG. 7 illustrates an example implementation of the process of FIG. 4 in accordance with an embodiment of the disclosure.

FIG. 7 illustrates an example implementation of the process of FIG. 4 in accordance with an embodiment of the disclosure. In FIG. 7, the process of FIG. 4 is performed at UE 1, which may be configured as UE 200 as described above with respect to FIGS. 2-3. Further, in the description of FIG. 7 below, reference is made to emergency health conditions #1, #2 and #3 as defined with respect to FIG. 6A for convenience of explanation. Further, with respect to FIG. 7, UE 1 is wirelessly connected to a set of health monitoring sensors that include at least a blood pressure monitor, a heart rate monitor, a glucose monitor and a brainwave detector.

Referring to FIG. 7, at block 700, UE 1 configures emergency health conditions #1, #2 and #3 (e.g., as discussed above with respect to block 400 of FIG. 4 and FIG. 5A). At block 705, UE 1 enters a restricted mode. In the embodiment of FIG. 7, assume that the restricted mode of UE 1 is configured to block Wi-Fi and cellular communicative functions (including LTE-D) as well as audio output (e.g., as in DND mode). At block 710, the set of health monitoring sensors (including the blood pressure monitor, heart rate monitor, glucose monitor and brainwave detector) provide health data to UE 1 (e.g., as in block 405 of FIG. 4), which is analyzed by the emergency health condition monitoring application 320 to determine whether any emergency health condition for the user of UE 1 exists.

Referring to FIG. 7, based on the health data from block 710, the emergency health condition monitoring application 320 at UE 1 detects that the user of UE 1 is currently experiencing emergency health condition #1 at block 715 (e.g., as in block 410 of FIG. 4). Based on the detection of emergency health condition #1, the restricted mode is at least partially disabled at block 720 (e.g., as in block 415 of FIG. 4). In an example, block 720 may occur based on the emergency health condition monitoring application 320 being verified as authorized to override the restricted mode as shown in restricted mode override utility screen 505B of FIG. 5B.

Because emergency health condition #1 is Level 1, the alarm reaction as defined in the alarm reaction configuration utility screen 605A of FIG. 6A is implemented at block 725 (e.g., as in block 420 of FIG. 4). In particular, UE 1 outputs an auditory alarm (e.g., to notify the user of the emergency health condition) and also transmits the alarm to contact Joe and the Family contact group. If one or more of Joe and the Family contact group members are all proximate to UE 1, then the alarm transmission can occur at least in part via a local or D2D wireless communication protocol (e.g., LTE-D, etc.). If one or more of Joe and the Family contact group members are remote, then the alarm transmission to any remote contact can occur at least in part via network mediation (e.g., the RAN 120, AP 125, etc.). Hence, network involvement is optional because it is possible that the alarm transmission can occur exclusively over the local or D2D wireless communication protocol. In this case, the restricted mode disablement of block 720 may be partial (e.g., the cellular communicative function can remain blocks since they are not necessary to implement the alarm reaction in this case).

Referring to FIG. 7, at some later point in time assume that the emergency health condition #1 detected at block 715 of the user is resolved (or at least acknowledged and dismissed) by the user of UE 1, such that UE 1 re-enters the restricted mode at block 730. At block 735, the set of health monitoring sensors (including the blood pressure monitor, heart rate monitor, glucose monitor and brainwave detector) continue to provide health data to UE 1 (e.g., as in block 405 of FIG. 4), which is analyzed by the emergency health condition monitoring application 320 to determine whether any emergency health condition for the user of UE 1 exists.

Referring to FIG. 7, based on the health data from block 735, the emergency health condition monitoring application 320 at UE 1 detects that the user of UE 1 is currently experiencing emergency health condition #2 at block 740 (e.g., as in block 410 of FIG. 4). Based on the detection of emergency health condition #2, the restricted mode is at least partially disabled at block 745 (e.g., as in block 415 of FIG. 4). In an example, block 745 may occur based on the emergency health condition monitoring application 320 being verified as authorized to override the restricted mode as shown in restricted mode override utility screen 505B of FIG. 5B.

Because emergency health condition #2 is Level 2, the alarm reaction as defined in the alarm reaction configuration utility screen 605B of FIG. 6B is implemented at block 750 (e.g., as in block 420 of FIG. 4). In particular, UE 1 outputs an auditory alarm (e.g., to notify the user of the emergency health condition), transmits the alarm to contact the Family contact group, broadcasts the alarm locally to any in-range UE (e.g., a distress signal that does not identify a specific target, and is rather intended to solicit help from any nearby person, even a stranger), and also calls emergency response personnel (e.g., via a cellular connection, etc.). In this case, the restricted mode may be fully disabled at block 745 to accommodate the Level 2 alarm reaction at block 750.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a DSP, an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods, sequences and/or algorithms described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal (e.g., UE). In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

While the foregoing disclosure shows illustrative embodiments of the disclosure, it should be noted that various changes and modifications could be made herein without departing from the scope of the disclosure as defined by the appended claims. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated.

What is claimed is:

1. A method of operating a user equipment (UE), comprising:

determining an emergency health condition for a user that is defined based on a set of health-related parameters crossing a corresponding set of thresholds;

receiving health data from a set of health monitoring sensors that are each configured to monitor one or more health-related parameters of the user;

detecting, based on execution of a given application at the UE while a restricted mode restricting access to a set of communicative functions of the UE is active, that the emergency health condition for the user exists based on the received health data indicating that the set of health-related parameters have crossed the corresponding set of thresholds;

verifying that the given application has permission to disable the restricted mode of the UE;

disabling the restricted mode in response to the detecting and the verifying; and conveying, using one or more communicative functions from the set of communicative functions that are made available by the disabling of the restricted mode, an alarm related to the detected emergency health condition for the user.

2. The method of claim 1, wherein the restricted mode is a do-not-disturb (DND) mode, a silent mode, a Wi-Fi-disabled mode and/or a cellular-disabled mode.

3. The method of claim 1,
wherein the set of health monitoring sensors includes a plurality of health monitoring sensors that are each associated with a different health-related parameter,
wherein the set of health-related parameters include each of the different health-related parameters of the plurality of health monitoring sensors.

4. The method of claim 1,
wherein the corresponding set of thresholds includes multiple thresholds for at least one health-related parameter in the set of health-related parameters,
wherein the multiple thresholds include an upper threshold and a lower threshold, and
wherein the detecting detects the emergency health condition based in part upon the at least one health-related parameter rising above the upper threshold or by falling below the lower threshold.

5. The method of claim 1, wherein the corresponding set of thresholds includes at least one user-defined threshold.

6. The method of claim 5, further comprising:
providing a user interface at the UE that allows the user to configure one or more of the corresponding set of thresholds for the set of health-related parameters,
wherein the at least one user-defined threshold is configured via the user interface.

7. The method of claim 1, further comprising:
providing a user interface at the UE that allows the user to configure which applications installed on the UE have permission to disable the restricted mode,
wherein the verifying is based upon whether the user grants permission to the given application via the user interface.

8. The method of claim 1, wherein the UE is coupled to at least one health monitoring sensor in the set of health monitoring sensors via a local wireless connection or a wired connection.

9. The method of claim 8, wherein the local wireless connection is a Bluetooth connection or a Near Field Communication (NFC) connection.

10. The method of claim 1,
wherein the conveying includes outputting the alarm by the UE locally, and/or wherein the conveying includes transmitting the alarm to one or more external devices.

11. The method of claim 1, further comprising:
maintaining a list of contacts to alert in response to a detection that the emergency health condition exists for the user,
wherein the conveying transmits the alarm to one or more external devices associated with one or more of the listed contacts.

12. The method of claim 11, wherein the conveying transmits the alarm to the one or more external devices via a device-to-device (D2D) connection or via a communications network.

13. The method of claim 11, further comprising:
providing a user interface at the UE that allows the user to configure the list of contacts to alert in response to a given detection that the emergency health condition exists for the user.

14. The method of claim 1, wherein the conveying includes broadcasting the alarm to any in-range UE via a wireless communications protocol.

15. The method of claim 14, wherein the wireless communications protocol is Long-Term Evolution Direct (LTE-D).

16. The method of claim 1, wherein the conveying includes transmitting the alarm to one or more emergency response personnel.

17. The method of claim 1, wherein the set of health monitoring sensors includes a blood pressure monitor, a heart rate monitor, a glucose monitor, a brainwave detector or any combination thereof.

18. The method of claim 1, wherein the set of health-related parameters includes blood pressure, heart rate, glucose level, brainwave activity or any combination thereof.

19. The method of claim 1,
wherein the disabling fully disables the restricted mode by making each communicative function in the set of communicative functions available, or
wherein the disabling partially disables the restricted mode by making less than all communicative functions in the set of communicative functions available.

20. The method of claim 1, wherein the one or more communicative functions include an audio output function of the UE, a vibratory output function of the UE, a wireless communicative function of the UE, or any combination thereof.

21. A user equipment (UE), comprising:
means for determining an emergency health condition for a user that is defined based on a set of health-related parameters crossing a corresponding set of thresholds;
means for receiving health data from a set of health monitoring sensors that are each configured to monitor one or more health-related parameters of the user;
means for detecting, based on execution of a given application at the UE while a restricted mode restricting access to a set of communicative functions of the UE is active, that the emergency health condition for the user exists based on the received health data indicating that the set of health-related parameters have crossed the corresponding set of thresholds;
means for verifying that the given application has permission to disable the restricted mode of the UE;
means for disabling the restricted mode in response to the detection and the verification; and
means for conveying, using one or more communicative functions from the set of communicative functions that are made available by the disabling of the restricted mode, an alarm related to the detected emergency health condition for the user.

22. The UE of claim 21, wherein the restricted mode is a do-not-disturb (DND) mode, a silent mode, a Wi-Fi-disabled mode and/or a cellular-disabled mode.

23. The UE of claim 21, wherein the means for conveying conveys the alarm by:
outputting the alarm by the UE locally,
transmitting the alarm to one or more external devices,
broadcasting the alarm to any in-range UE via a wireless communications protocol,
transmitting the alarm to emergency response personnel, or
any combination thereof.

24. A user equipment (UE), comprising:
at least one processor coupled to memory and configured to:
determine an emergency health condition for a user that is defined based on a set of health-related parameters crossing a corresponding set of thresholds;
receive health data from a set of health monitoring sensors that are each configured to monitor one or more health-related parameters of the user;
detect, based on execution of a given application at the UE while a restricted mode restricting access to a set of communicative functions of the UE is active, that the emergency health condition for the user exists based on the received health data indicating that the set of health-related parameters have crossed the corresponding set of thresholds;
verify that the given application has permission to disable the restricted mode of the UE;
disable the restricted mode in response to the detection and the verification; and
convey, using one or more communicative functions from the set of communicative functions that are made available by the disabling of the restricted mode, an alarm related to the detected emergency health condition for the user.

25. The UE of claim 24, wherein the restricted mode is a do-not-disturb (DND) mode, a silent mode, a Wi-Fi-disabled mode and/or a cellular-disabled mode.

26. The UE of claim 24, wherein the at least one processor conveys the alarm by:
outputting the alarm by the UE locally,
transmitting the alarm to one or more external devices,
broadcasting the alarm to any in-range UE via a wireless communications protocol,
transmitting the alarm to emergency response personnel, or
any combination thereof.

27. A non-transitory computer-readable medium containing instructions stored thereon, which, when executed by a user equipment (UE), cause the UE to perform operations, the instructions comprising:
at least one instruction to cause the UE to determine an emergency health condition for a user that is defined based on a set of health-related parameters crossing a corresponding set of thresholds;
at least one instruction to cause the UE to receive health data from a set of health monitoring sensors that are each configured to monitor one or more health-related parameters of the user;
at least one instruction to cause the UE to detect, based on execution of a given application at the UE while a restricted mode restricting access to a set of communicative functions of the UE is active, that the emergency health condition for the user exists based on the received health data indicating that the set of health-related parameters have crossed the corresponding set of thresholds;

at least one instruction to cause the UE to verify that the given application has permission to disable the restricted mode of the UE;

at least one instruction to cause the UE to disable the restricted mode in response to the detection and the verification; and at least one instruction to cause the UE to convey, using one or more communicative functions from the set of communicative functions that are made available by the disabling of the restricted mode, an alarm related to the detected emergency health condition for the user.

28. The non-transitory computer-readable medium of claim 27, wherein the restricted mode is a do-not-disturb (DND) mode, a silent mode, a Wi-Fi-disabled mode and/or a cellular-disabled mode.

29. The non-transitory computer-readable medium of claim 27, wherein the at least one instruction to cause the UE to convey causes the UE to convey the alarm by:

outputting the alarm by the UE locally, transmitting the alarm to one or more external devices, broadcasting the alarm to any in-range UE via a wireless communications protocol, transmitting the alarm to emergency response personnel, or any combination thereof.

* * * * *